United States Patent
Yamaguchi et al.

(10) Patent No.: US 9,487,726 B2
(45) Date of Patent: Nov. 8, 2016

(54) IMIDE COMPOUND, METHOD FOR PRODUCING SAME, THICKENING AGENT FOR GREASE, AND GREASE COMPOSITION

(75) Inventors: Kentaro Yamaguchi, Tokyo (JP); Osamu Kurosawa, Tokyo (JP); Miki Fujiwara, Tokyo (JP); Ryuichi Ueno, Tokyo (JP)

(73) Assignee: JX NIPPON OIL & ENERGY CORPORATION, Tokyo (JP)

( * ) Notice: Subject to any disclaimer, the term of this patent is extended or adjusted under 35 U.S.C. 154(b) by 271 days.

(21) Appl. No.: 13/978,455

(22) PCT Filed: Jan. 6, 2012

(86) PCT No.: PCT/JP2012/050206
§ 371 (c)(1),
(2), (4) Date: Sep. 6, 2013

(87) PCT Pub. No.: WO2012/093731
PCT Pub. Date: Jul. 12, 2012

(65) Prior Publication Data
US 2013/0345102 A1 Dec. 26, 2013

(30) Foreign Application Priority Data
Jan. 6, 2011 (JP) .................. 2011-001450

(51) Int. Cl.
*C10M 115/08* (2006.01)
*C10M 133/16* (2006.01)
(Continued)

(52) U.S. Cl.
CPC .......... *C10M 115/08* (2013.01); *C07D 209/48* (2013.01); *C07D 307/89* (2013.01);
(Continued)

(58) Field of Classification Search
CPC ............ C10M 115/08; C10M 133/16; C10M 2207/142; C10M 2215/04; C10M 2215/06; C10M 2215/0813; C10M 2215/086; C10N 2230/08; C10N 2250/10; C07D 209/48; C07D 307/89; C07D 487/04; C07D 493/04

USPC .......................................... 508/288; 548/416
See application file for complete search history.

(56) References Cited

U.S. PATENT DOCUMENTS

| 3,025,241 A | 3/1962 | Dreher et al. |
| 3,093,656 A * | 6/1963 | Goodrich et al. ............ 548/433 |

(Continued)

FOREIGN PATENT DOCUMENTS

| JP | S54-113605 | 9/1979 |
| JP | S57-109896 | 7/1982 |

(Continued)

OTHER PUBLICATIONS

International Search Report for International Application No. PCT/JP2012/050206, which was mailed on Feb. 7, 2012.
(Continued)

*Primary Examiner* — James Goloboy
(74) *Attorney, Agent, or Firm* — Greenblum & Bernstein, P.L.C.

(57) ABSTRACT

The present invention provides an imide compound represented by the following general formula (1). The imide compound of the present invention, particularly when used as a thickening agent for grease, is excellent in durability at high temperatures.

[Chemical Formula 1]

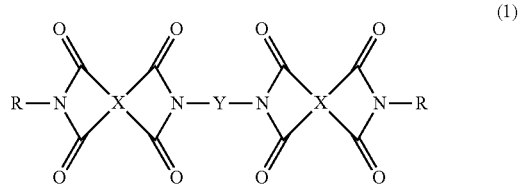

[wherein X represents a tetravalent residue obtained by removing four carboxylic groups from an aromatic tetracarboxylic acid, Y represents a divalent residue obtained by removing two amino groups from an aliphatic diamine or an aromatic diamine, and R represents a residue obtained by removing an amino group from an aliphatic monoamine, an alicyclic monoamine, or an aromatic monoamine.]

4 Claims, 1 Drawing Sheet

(51) Int. Cl.
| | |
|---|---|
| C07D 487/04 | (2006.01) |
| C07D 493/04 | (2006.01) |
| C07D 209/48 | (2006.01) |
| C07D 307/89 | (2006.01) |

(52) U.S. Cl.
CPC ........... *C07D487/04* (2013.01); *C07D 493/04* (2013.01); *C10M 133/16* (2013.01); *C10M 2207/142* (2013.01); *C10M 2215/04* (2013.01); *C10M 2215/06* (2013.01); *C10M 2215/086* (2013.01); *C10M 2215/0813* (2013.01); *C10N 2230/08* (2013.01); *C10N 2250/10* (2013.01)

(56) References Cited

U.S. PATENT DOCUMENTS

| | | | |
|---|---|---|---|
| 5,346,979 A | | 9/1994 | Okinoshima et al. |
| 2012/0316091 A1* | | 12/2012 | Kawamura .................. 508/100 |

FOREIGN PATENT DOCUMENTS

| | | |
|---|---|---|
| JP | 2003-342593 | 12/2003 |
| JP | 2004-359809 | 12/2004 |
| JP | 2008-231310 | 10/2008 |
| JP | 2009-197162 | 9/2009 |
| JP | 2010-077320 | 4/2010 |
| WO | WO 2011102441 A1 * | 8/2011 |

OTHER PUBLICATIONS

English translation of the International Preliminary Report on Patentability for International Application No. PCT/JP2012/050206, which was mailed on Jul. 18, 2013.

T. Matsumoto, "The Origin of Coloration in Aromatic Polyimides-an Approach from Quantum Chemistry," Journal of Photopolymer Science and Technology, 1999, vol. 12, No. 2, p. 231-236.

Vysokomolekulyarnye Soedieniya, Seria A, 1976, vol. 18, No. 11, p. 2452-2460.

Chemical Abstracts, 1973, vol. 78, No. 4, p. 17, right column, 16682v.

Kagan, G.I. et al., *Quantum-Mechanical Investigation of Some Oligomeric Heteroaromatic Compounds*, translated from Khimiya Geterotsiklicheskikh Soedinenii, No. 8, pp. 1048-1056, Aug. 1972.

Extended European Search Report for Application No. 12732412.7, which was mailed on Aug. 24, 2015.

* cited by examiner

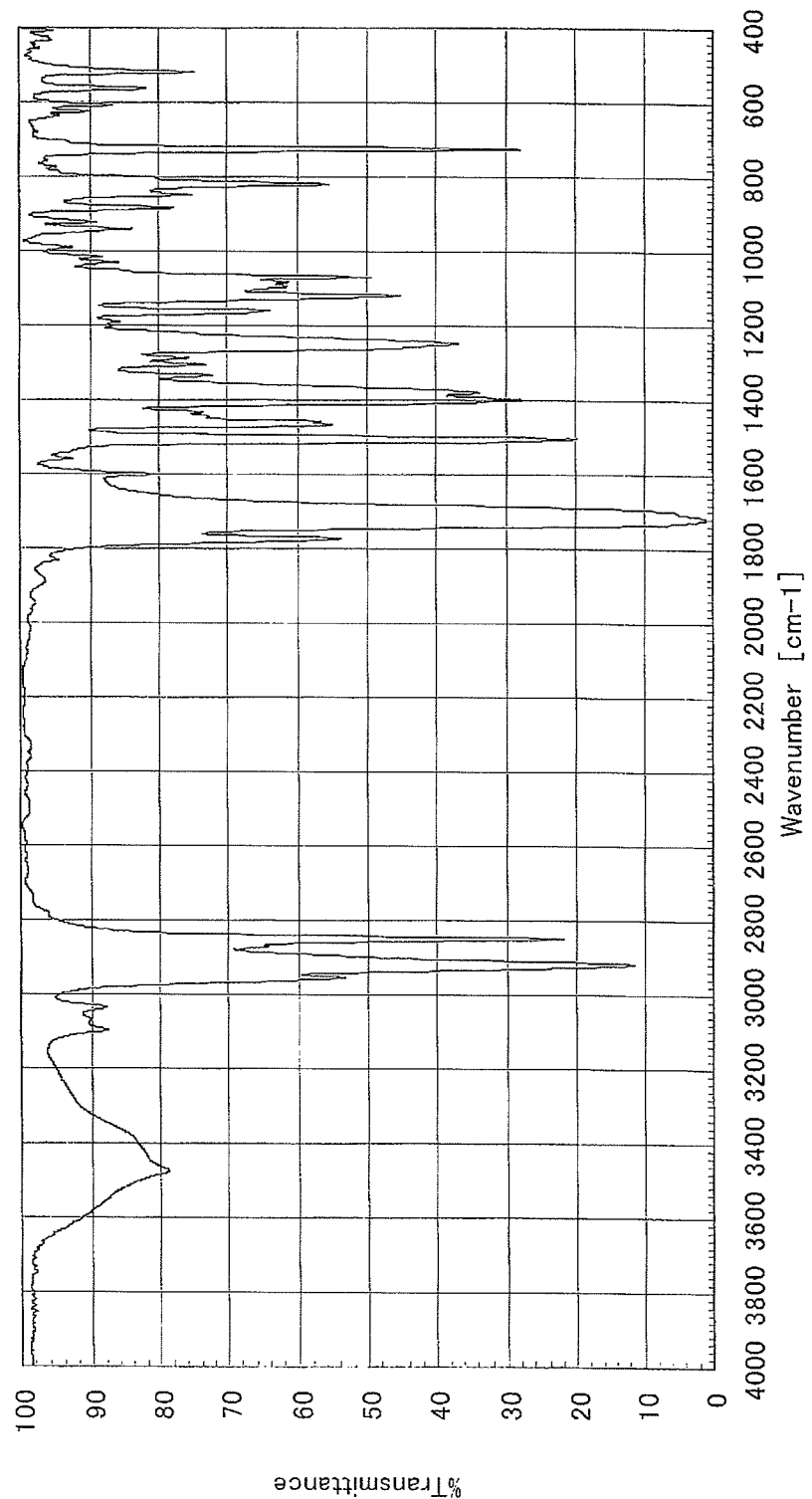

IMIDE COMPOUND, METHOD FOR PRODUCING SAME, THICKENING AGENT FOR GREASE, AND GREASE COMPOSITION

TECHNICAL FIELD

The present invention relates to an imide compound, a method for producing the same, a thickening agent for grease, and a grease composition.

BACKGROUND ART

In automobiles, reduction of the engine room space is progressing in response to conversion to Front Wheel Drive (FF) for the purpose of achieving size and weight reduction and to a demand for a larger interior space. Size and weight reduction of every component in an engine room is required for reduction of the engine room space, and thus achieving further size and weight reduction is being advanced in the aforementioned electrical parts and engine accessories. Meanwhile, higher performance and greater output are also being required of electrical parts and engine accessories. However, decrease in output with smaller size is unavoidable, and for example, in alternators and electromagnetic clutches for automotive air conditioners, decrease in output is compensated for by increasing their speed. Accordingly, idler pulleys speed up as well, and heat generation is promoted at lubricated points. Additionally, hermeticity of engine rooms is accelerated in order to improve silence during engine operation, and in this case, increase in temperature in such engine rooms is promoted as well.

Moreover, double row angular contact ball bearings have been used as bearings for compressor pulleys and magnetic clutches for automotive air conditioners, but nowadays, the tendency is that single row bearings are used for lighter weight and lower cost of the pulleys and the clutches. As for a single row ball bearing used under the same conditions as double row angular contact ball bearing, due to its larger PV value (a product of the bearing surface pressure P and the slip velocity V), which represents the load capacity limit of the bearing, smaller bearing space volume, and the like, the tendency is that the bearing is used under a condition that the grease filling amount is small and the grease heat generation amount is large.

Thus, since the use conditions of the electrical parts and engine accessories become increasingly severer, improvement in its durability particularly at high temperatures has been necessary for grease to be applied to these roller bearings.

In Patent Literatures 1 to 5, grease compositions in which a urea thickening agent is used are disclosed as conventional grease.

In Patent Literatures 6 to 7, grease compositions in which an imide thickening agent is used are disclosed as well.

CITATION LIST

Patent Literature

Patent Literature 1: Japanese Patent Application Laid-Open No. 2004-359809
Patent Literature 2: Japanese Patent Application Laid-Open No. 2003-342593
Patent Literature 3: Japanese Patent Application Laid-Open No. 2010-077320
Patent Literature 4: Japanese Patent Application Laid-Open No. 2009-197162
Patent Literature 5: Japanese Patent Application Laid-Open No. 2008-231310
Patent Literature 6: Japanese Patent Application Laid-Open No. 54-113605
Patent Literature 7: Japanese Patent Application Laid-Open No. 57-109896

SUMMARY OF INVENTION

Technical Problem

The present invention aims to provide a novel imide compound, particularly an imide compound excellent in durability at high temperatures when used as a thickening agent for grease, and a method for producing the same. Additionally, another object of the present invention aims to provide a thickening agent for grease and a grease composition in which the imide compound is used.

Solution to Problem

The present invention provides an imide compound represented by the following general formula (1):

[Chemical Formula 1]

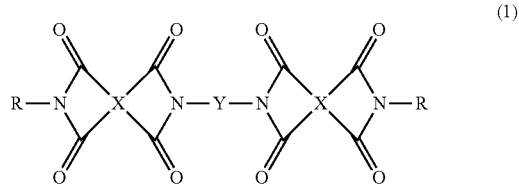

(1)

[wherein X represents a tetravalent residue obtained by removing four carboxylic groups from an aromatic tetracarboxylic acid, Y represents a divalent residue obtained by removing two amino groups from an aliphatic diamine or an aromatic diamine, and R represents a residue obtained by removing an amino group from an aliphatic monoamine, an alicyclic monoamine, or an aromatic monoamine.]

The present invention also provides a method for producing an imide compound comprising:
a first step of reacting an aromatic tetracarboxylic dianhydride represented by the following general formula (2) with a diamine represented by the following general formula (3) to obtain a reaction intermediate represented by the following general formula (4); and
a second step of reacting the reaction intermediate with a monoamine represented by the following general formula (5) to obtain the imide compound represented by the above general formula (1):

[Chemical Formula 2]

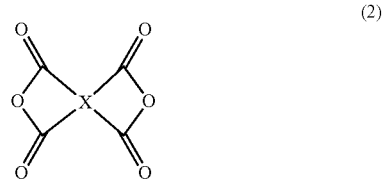

(2)

-continued

[Chemical Formula 3]

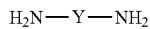
(3)

[Chemical Formula 4]

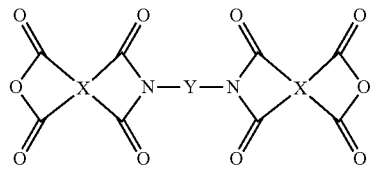
(4)

[Chemical Formula 5]

(5)

[wherein X represents a tetravalent residue obtained by removing four carboxylic groups from an aromatic tetracarboxylic acid, Y represents a divalent residue obtained by removing two amino groups from an aliphatic diamine or an aromatic diamine, and R represents a residue obtained by removing an amino group from an aliphatic monoamine, an alicyclic monoamine, or an aromatic monoamine.]

Furthermore, the present invention provides a thickening agent for grease containing at least one imide compound, wherein the proportion of the imide compound represented by the above general formula (1) is 30% by mass or more in the total mass of the imide compounds.

Moreover, the present invention provides a grease composition—containing a lubricant base oil and the imide compound represented by—the above general formula (1), wherein the content of the imide compound is 2 to 50% by mass based on the total amount of the grease composition.

In this context, according to the consideration of the inventors, for grease compositions in which a urea thickening agent is used, as disclosed in Patent Literatures 1 to 7, it was proved that adequate durability cannot be obtained depending on use environments, such as when used at high temperatures. In contrast to this, the inventors confirm that an imide compound, a thickening agent for grease and a grease composition of the present invention are able to exert adequate durability even when used at high temperatures.

Advantageous Effects of Invention

As described above, according to the present invention, it becomes possible to provide a novel imide compound, particularly an imide compound excellent in durability at high temperatures when used as a thickening agent for grease, and a method for producing the same.

According to the present invention, it also becomes possible to provide a thickening agent for grease and a grease composition that can exert adequate durability even when used at high temperatures.

BRIEF DESCRIPTION OF DRAWINGS

FIG. 1 is a diagram showing the infrared absorption spectrum of the imide compound obtained in Example 1.

DESCRIPTION OF EMBODIMENTS

Hereinafter, preferable embodiments of the present invention will be described in detail.

First Embodiment

Imide Compound

An imide compound according to a first embodiment of the invention has a structure represented by the following general formula (1). That is, the imide compound of the invention is a compound having four imide groups.

[Chemical Formula 6]

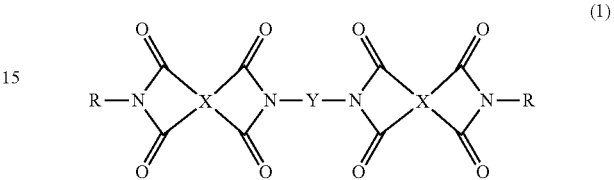
(1)

X is a tetravalent residue obtained by removing four carboxylic groups from an aromatic tetracarboxylic acid. Aromatic tetracarboxylic acids are defined as compounds in which four carboxylic groups are added to an aromatic hydrocarbon or a heterocyclic compound, or derivatives thereof. Examples of the aromatic tetracarboxylic dianhydride monomers from which the structure X is derived include, but not limited to, the following: pyromellitic dianhydride, 1,2,3,4-benzenetetracarboxylic dianhydride, 2,3,5,6-pyridinetetracarboxylic dianhydride, 2,3,4,5-thiophenetetracarboxylic dianhydride, 2,2',3,3'-benzophenonetetracarboxylic dianhydride, 2,3',3,4'-benzophenonetetracarboxylic dianhydride, 3,3',4,4'-benzophenonetetracarboxylic dianhydride, 2,2',3,3'-biphenyltetracarboxylic dianhydride, 3,3',4,4'-biphenyltetracarboxylic dianhydride, 2,3,3',4'-biphenyltetracarboxylic dianhydride, 3,3',4,4'-p-terphenyltetracarboxylic dianhydride, 2,2',3,3'-p-terphenyltetracarboxylic dianhydride, 2,3,3',4'-p-terphenyltetracarboxylic dianhydride, 1,2,4,5-naphthalenetetracarboxylic dianhydride, 1,2,5,6-naphthalenetetracarboxylic dianhydride, 1,2,6,7-naphthalenetetracarboxylic dianhydride, 1,4,5,8-naphthalenetetracarboxylic dianhydride, 2,3,6,7-naphthalenetetracarboxylic dianhydride, 2,3,6,7-anthracenetetracarboxylic dianhydride, 1,2,5,6-anthracenetetracarboxylic dianhydride, 1,2,6,7-phenanthrenetetracarboxylic dianhydride, 1,2,7,8-phenanthrenetetracarboxylic dianhydride, 1,2,9,10-phenanthrenetetracarboxylic dianhydride, 3,4,9,10-perylenetetracarboxylic dianhydride, 2,6-dichloronaphthalene-1,4,5,8-tetracarboxylic dianhydride, 2,7-dichloronaphthalene-1,4,5,8-tetracarboxylic dianhydride, 2,3,6,7-tetrachloronaphthalene-1,4,5,8-tetracarboxylic dianhydride, 1,4,5,8-tetrachloronaphthalene-2,3,6,7-tetracarboxylic dianhydride, bis(2,3-dicarboxyphenyl)ether dianhydride, bis(3,4-dicarboxyphenyl)ether dianhydride, bis(2,3-dicarboxyphenyl)methane dianhydride, bis(3,4-dicarboxyphenyl)methane dianhydride, bis(2,3-dicarboxyphenyl)sulfone dianhydride, bis(3,4-dicarboxyphenyl)sulfone dianhydride, 1,1-bis(2,3-dicarboxyphenyl)ethane dianhydride, 1,1-bis(3,4-dicarboxyphenyl)ethane dianhydride, 2,2-bis(2,3-dicarboxyphenyl)propane dianhydride, 2,2-bis(3,4-dicarboxyphenyl)propane dianhydride, 2,6-bis(3,4-dicarboxyphenoxy)pyridine dianhydride, 1,1,1,3,3,3-hexafluoro-2,2-bis(3,4-dicarboxyphenyl)propane dianhydride, bis(3,4-dicarboxyphenyl)dimethylsilane dianhydride, bis(3,4-dicarboxyphenyl)methylphenylsilane dianhydride, bis(3,4-dicarboxyphenyl)diphenylsilane dianhydride, bis(3,4-dicarboxyphenyl)-1,1,3,3-tetramethyldisiloxane dianhydride, or mixtures thereof.

As the aromatic tetracarboxylic acid from which the structure X is derived, compounds in which four carboxylic acids are bound to an aromatic hydrocarbon group, particularly, (a) 1,2,4,5-benzenetetracarboxylic acid or derivatives thereof and (b) compounds having two 3,4-dicarboxyphenyl groups are preferred. Additionally, as (b) the compounds having two 3,4-dicarboxyphenyl groups, (b-1) compounds having a structure in which two dicarboxyphenyl groups are directly bound to each other and (b-2) compounds having a structure in which two dicarboxyphenyl groups are bound via a linking group of which constituent atom number is one or two are particularly preferred.

Y is a divalent residue obtained by removing two amino groups from an aliphatic diamine or an aromatic diamine. Examples of the diamines from which the structure Y is derived include, but not limited to, aliphatic diamines, aromatic diamines, and mixtures thereof Examples of the aliphatic diamines include saturated or unsaturated, linear, branched, or alicyclic hydrocarbon groups, specifically methylenediamine, ethylenediamine, trimethylenediamine, tetramethylenediamine, pentamethylenediamine, hexamethylenediamine, 2,5-dimethylhexamethylenediamine, 3-methoxyhexamethylenediamine, heptamethylenediamine, 2,5-dimethylheptamethylenediamine, 3-methylheptamethylenediamine, 4,4-dimethylheptamethylenediamine, octamethylenediamine, nonamethylenediamine, 5-methylnonamethylenediamine, decamethylenediamine, 1,4-diaminocyclohexane, 1,3-bis(aminomethyl)cyclohexane, 1,4-bis(aminomethyl)cyclohexane, 4,4'-methylenebis(cyclohexylamine), 4,4'-methylenebis(2-methylcyclohexylamine), bis(aminomethyl)norbornane, 1,3-diaminoadamantane, isophoronediamine, and 1,8-diamino-p-menthane.

Examples of the aromatic diamines include meta-phenylenediamine, p-phenylenediamine, 1,4-diaminonaphthalene, 1,5-diaminonaphthalene, 1,8-diaminonaphthalene, 2,6-diaminonaphthalene, 2,7-diaminonaphthalene, 1,8-diaminoanthracene, 2,6-diaminoanthracene, 2,7-diaminoanthracene, 2,4-diaminotoluene, 2,5-diamino(meta-xylene), 1,1-bis(3-aminophenyl)ethane, 1,1-bis(4-aminophenyl)ethane, 2,2-bis(3-aminophenyl)propane, 2,2-bis(4-aminophenyl)propane, 2,2-bis(4-amino-3,5-dimethylphenyl)propane, 2,5-diaminopyridine, 2,6-diaminopyridine, 3,5-diaminopyridine, 2,4-diaminotoluenebenzidine, 3,3'-diaminobiphenyl, 3,3'-dichlorobenzidine, 3,3'-dimethylbenzidine, 3,3'-dimethoxybenzidine, 3,5-diaminobenzoic acid, 2,2'-diaminobenzophenone, 4,4'-diaminobenzophenone, 3,3'-diaminodiphenyl ether, 4,4'-diaminodiphenyl ether, 3,3'-diaminodiphenylmethane, 4,4'-diaminodiphenylmethane, 4,4'-diamino-3,3',5,5'-tetramethyldiphenylmethane, 3,3'-diaminodiphenyl sulfone, 4,4'-diaminodiphenyl sulfone, 3,3'-diaminodiphenyl sulfide, 4,4'-diaminodiphenyl sulfide, 4,4'-diaminodiphenyl thioether, 4,4'-diamino-3,3',5,5'-tetramethyldiphenyl ether, 4,4'-diamino-3,3',5,5'-tetraethyldiphenyl ether, 1,3-bis(3-aminophenoxy)benzene, 1,3-bis(4-aminophenoxy)benzene, 1,4-bis(3-aminophenoxy)benzene, 1,4-bis(4-aminophenoxy)benzene, 2,6-bis(3-aminophenoxy)pyridine, 1,4-bis(3-aminophenylsulfonyl)benzene, 1,4-bis(4-aminophenylsulfonyl)benzene, 1,4-bis(3-aminophenyl thioether)benzene, 1,4-bis(4-aminophenyl thioether)benzene, 4,4'-bis(3-aminophenoxy)diphenylsulfone, 4,4'-bis(4-aminophenoxy)diphenylsulfone, bis(4-aminophenyl)amine, bis(4-aminophenyl)-N-methylamine, bis(4-aminophenyl)-N-phenylamine, bis(4-aminophenyl)phosphine oxide, 4,4'-bis(4-aminophenoxy)biphenyl, bis[4-(3-aminophenoxy)phenyl]sulfone, bis[4-(4-aminophenoxy)phenyl]sulfone, bis[4-(4-aminophenoxy)phenyl]ether, bis[4-(4-aminophenoxy)phenyl]methane, bis[3-methyl-4-(4-aminophenoxy)phenyl]methane, bis[3-chloro-4-(4-aminophenoxy)phenyl]methane, bis[3,5-dimethyl-4-(4-aminophenoxy)phenyl]methane, 1,1-bis[4-(4-aminophenoxy)phenyl]ethane, 1,1-bis[3-methyl-4-(4-aminophenoxy)phenyl]ethane, 1,1-bis[3-chloro-4-(4-aminophenoxy)phenyl]ethane, 1,1-bis[3,5-dimethyl-4-(4-aminophenoxy)phenyl]ethane, 2,2-bis[4-(4-aminophenoxy)phenyl]propane, 2,2-bis[3-methyl-4-(4-aminophenoxy)phenyl]propane, 2,2-bis[3-chloro-4-(4-aminophenoxy)phenyl]propane, 2,2-bis[3,5-dimethyl-4-(4-aminophenoxy)phenyl]propane, 2,2-bis[4-(4-aminophenoxy)phenyl]butane, 2,2-bis[3-methyl-4-(4-aminophenoxy)phenyl]butane, 2,2-bis[3,5-dimethyl-4-(4-aminophenoxy)phenyl]butane, 2,2-bis[3,5-dibromo-4-(4-aminophenoxy)phenyl]butane, 1,1,1,3,3,3-hexafluoro-2,2-bis(4-aminophenyl)propane, 1,1,1,3,3,3-hexafluoro-2,2-bis[3-methyl-4-(4-aminophenoxy)phenyl]propane, bis(3-aminophenyl)tetramethyldisilane, bis(4-aminophenyl)tetramethyldisilane, bis(3-methyl-4-aminophenyl)tetramethyldisilane, bis(3-aminophenoxy)tetramethyldisilane, bis(4-aminophenoxy)tetramethyldisilane, bis(3-aminophenoxy)-1,1,3,3-tetramethyldisiloxane, and bis(4-aminophenoxy)-1,1,3,3-tetramethyldisiloxane.

As the diamine from which the structure Y is derived, (c) compounds in which amino groups are bound to both ends of a linear aliphatic hydrocarbon, (d) compounds having two aminophenyl groups, and (e) phenylenediamines or derivatives thereof are preferred. Moreover, as (c) the compounds in which amino groups are bound to both ends of a linear aliphatic hydrocarbon, compounds in which amino groups are bound to both ends of a linear aliphatic hydrocarbon with the carbon number from 2 to 10 are particularly preferred. Furthermore, as (d) the compounds having two aminophenyl groups, (d-1) compounds having a structure in which two aminophenyl groups are directly bound to each other and (d-2) compounds having a structure in which two aminophenyl groups are bound via a linking group of which constituent atom number is one or two are particularly preferred because they are excellent in heat resistance.

R is a residue obtained by removing an amino group from an aliphatic monoamine, an alicyclic monoamine, or an aromatic monoamine. Examples of the monoamines from which the structure R is derived include, but not limited to, the following monoamines and mixture thereof.

Examples of the monoamines include aliphatic amines, alicyclic amines, or aromatic amines, have a hydrocarbon group with the carbon number from 6 to 20 and preferably from 8 to 18, and include linear or branched chain alkylamines, linear or branched chain alkenylamines, cycloalkylamines, alkylcycloalkylamines, arylamines, alkylarylamines, and arylalkylamines. Specific examples include linear or branched chain alkylamines, such as, hexylamine, heptylamine, octylamine, nonylamine, decylamine, undecylamine, dodecylamine, tridecylamine, tetradecylamine, pentadecylamine, hexadecylamine, heptadecylamine, octadecylamine, nonadecylamine, and eicosylamine; cyclohexylamine; alkylcycloalkylamines, such as methylcyclohexylamine, dimethylcyclohexylamine, ethylcyclohexylamine, diethylcyclohexylamine, propylcyclohexylamine, isopropylcyclohexylamine, 1-methyl-3-propylcyclohexylamine, butylcyclohexylamine, amylcyclohexylamine, amylmethylcyclohexylamine, hexylcyclohexylamine, heptylcyclohexylamine, octylcyclohexylamine, nonylcyclohexylamine, decylcyclohexylamine, undecylcyclohexylamine, dodecylcyclohexylamine, tridecylcyclohexylamine, and tetradecylcyclohexylamine; arylamines, such as phenylamine and naphthylamine; alkylarylamines, such as tolylamine, ethylphenylamine, xylylamine, propylphenylamine, cumenylamine, methylnaphthylamine, ethylnaphthylamine, dimethylnaphthylamine, and propylnaphthylamine; arylalkylamines, such as benzylamine, methylbenzylamine, and ethylbenzylamine.

Among the monoamines from which the structure R is derived, aliphatic amines are preferred from the viewpoint of lubricity and grease performance. The carbon number of the aliphatic amines is preferably from 4 to 20, and more preferably from 8 to 20. In this context, the aliphatic amines may be either saturated aliphatic amines or unsaturated aliphatic amines, but saturated aliphatic amines are preferred because they are excellent in oxidization stability.

In contrast, alicyclic amines are preferred from the viewpoint of heat resistance. The carbon number of the alicyclic amine is preferably from 4 to 20 and more preferably from 4 to 10. In this context, the alicyclic amine may be either saturated alicyclic amines or unsaturated alicyclic amines, but saturated alicyclic amines are preferred because they are excellent in oxidization stability.

Alternatively, aromatic amines are preferred from the viewpoint of heat resistance. The carbon number of the aromatic amine is preferably from 6 to 20 and more preferably from 6 to 18.

Second Embodiment

Method for Producing an Imide Compound

A method for producing an imide compound according to the second embodiment of the present invention comprises:
a first step of reacting an aromatic tetracarboxylic dianhydride represented by the following general formula (2) with a diamine represented by the following general formula (3) to obtain a reaction intermediate represented by the following general formula (4); and
a second step of reacting the reaction intermediate with a monoamine represented by the following general formula (5) to obtain the imide compound represented by the above general formula (1):

[Chemical Formula 7]

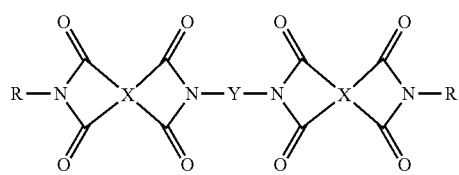
(1)

[Chemical Formula 8]

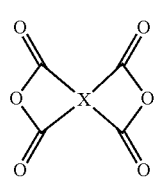
(2)

[Chemical Formula 9]

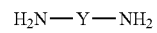
(3)

[Chemical Formula 10]

(4)

[Chemical Formula 11]

(5)

[wherein X represents a tetravalent residue obtained by removing four carboxylic groups from an aromatic tetracarboxylic acid, Y represents a divalent residue obtained by removing two amino groups from an aliphatic diamine or an aromatic diamine, and R represents a residue obtained by removing an amino group from an aliphatic monoamine, an alicyclic monoamine, or an aromatic monoamine.]

A preferable example of the method for producing an imide compound according to this embodiment will be described with referring to the following reaction scheme.

[Chemical Formula 12]

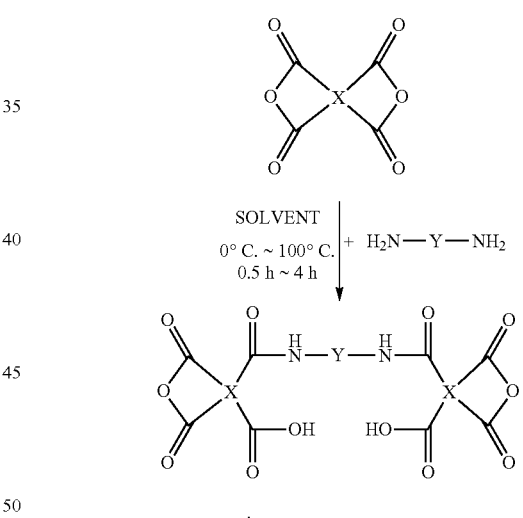

-continued

100° C. ~ 350° C.
0.5 h ~ 10 h

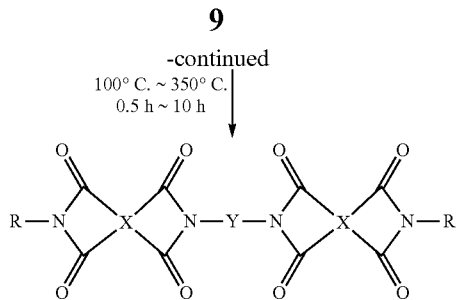

In the first step, it is preferred that the charge ratio of the tetracarboxylic dianhydride represented by the general formula (2) to the diamine represented by the general formula (3) is preferably 1.6 to 2.4 mol and particularly 1.9 to 2.1 mol of the tetracarboxylic dianhydride represented by the general formula (2) per mol of the diamine represented by the general formula (3). In this context, it is preferred that the reaction temperature is 100° C. to 350° C. and particularly 130° C. to 260° C. By reacting at such temperatures, the reaction intermediate represented by the general formula (4) can be obtained by cyclodehydration at a high yield. It is preferred that the reaction is performed at 100° C. to 350° C., and particularly at 130° C. to 260° C., after reacting initially at 0° C. to 100° C. The preferable reaction time is 0.5 to 6 hours and particularly 1 to 4 hours.

The reaction of the tetracarboxylic dianhydride represented by the general formula (2) with the diamine represented by the general formula (3) in the first step can be performed in a solvent. Organic solvents, such as N-methyl-2-pyrrolidone, dimethylformamide, dimethyl sulfoxide, acetone, tetrahydrofuran, and toluene, or mixed solvents of two or more of them can be used as the solvent.

In this context, if a solvent is used, the reaction mixture containing the reaction intermediate represented by the general formula (4) and the solvents can be supplied as is, after the first step, to the second step described below. In other words, by adding the monoamine represented by the general formula (5) to the reaction intermediate after the first step, the reaction intermediate represented by the general formula (4) can be reacted with the monoamine represented by the general formula (5).

Although the amount of the monoamine represented by the general formula (5) used in the second step is not particularly restricted, it is preferred to use 1.2 to 2.8 mol, particularly 1.6 to 2.4 mol, and more particularly 1.8 to 2.2 mol of the monoamine represented by the general formula (5) per mol of the diamine represented by the general formula (3). Additionally, in this context, X, Y, and R referred to herein are the same as X, Y, and R in the general formula (1), and the solvent to be used is organic solvents such as N-methyl-2-pyrrolidone, dimethylformamide, dimethyl sulfoxide, acetone, tetrahydrofuran, and toluene, or combinations thereof.

In this context, it is preferred that the reaction with monoamine is performed at 100° C. to 350° C. and particularly at 130° C. to 260° C. after reacting initially at 0° C. to 100° C. By reacting at such temperatures, the purity of imide compound represented by the general formula (1) can be increased by cyclodehydration. The preferable reaction time is 0.5 to 10 hours and particularly 2 to 8 hours.

Third Embodiment

Thickening Agent for Grease

A thickening agent for grease according to a third embodiment of the invention is one that contains at least one imide compound, wherein the proportion of the imide compound represented by the above general formula (1) is 30% by mass or more in the total mass of the imide compounds. Additionally, it may further contain imide compounds other than the imide compound represented by the above general formula (1).

The thickening agent for grease according to this embodiment may contain imide compounds other than the imide compound represented by the above general formula (1), but the proportion of the imide compound represented by the above general formula (1) is 30% by mass or more as mentioned above and preferably 50% by mass or more in the total of all the imide compounds contained in the thickening agent for grease. High heat-resistant grease can be obtained by increasing the proportion of the compound represented by the general formula (1) up to 30% by mass or more.

Since the imide compound according to the first embodiment and the thickening agent for grease according to the third embodiment are excellent in heat resistance, they are particularly preferably used as thickening agents for grease for constant velocity gears, variable velocity gears, steel-making facilities, ball bearings, roller bearings to be used at high temperatures, and the like. The operating temperatures for these applications are preferably −40° C. to 300° C. and more preferably −40° C. to 250° C.

Fourth Embodiment

Grease Composition

A grease composition according to the fourth embodiment is one that contains a lubricant base oil and the imide compound represented by the above general formula (1), wherein the content of the imide compound is 2 to 50% by mass based on the total amount of the grease composition.

In the grease composition according to this embodiment, the content of the above imide compound is 2% by mass or more, preferably 5% by mass or more, and also 50% by mass or less, preferably 40% by mass or less based on the total amount of the grease composition. The composition does not adequately become greasy when the content of the imide compound is less than 2% by mass because the effect of the thickening agent is small. In contrast, the composition cannot exert a sufficient lubricant performance when the content of the imide compound is more than 50% by mass because it becomes too stiff for grease. Each of the contents is not preferable.

Examples of the lubricant base oils for the grease composition of the present invention include mineral oils and/or synthetic oils.

Examples of such mineral oils include those obtained by the method usually performed in the process for producing lubricants in the petroleum refining industry, for example, those refined by subjecting the lubricant fraction obtained by distillating crude oil under the normal pressure or a reduced pressure to one or more treatments such as, solvent deasphalting, solvent extraction, hydrocracking, solvent dewaxing, contact dewaxing, hydrorefining, sulfuric acid washing, clay treatment, and the like.

Additionally, specific examples of synthetic oils include poly α-olefins or hydrides thereof, such as polybutene, 1-octene oligomers, and 1-decene oligomers; diesters, such as ditridecyl glutarate, di 2-ethylhexyl adipate, diisodecyl adipate, ditridecyl adipate, and di 3-ethylhexyl sebacate; polyol esters, such as trimethylolpropane caprylate, trimethylolpropane pelargonate, pentaerythritol 2-ethyl hexanoate, and pentaerythritol pelargonate; alkylnaphthalenes; alkylbenzenes, polyoxyalkylene glycols; polyphenyl ethers; dialkyl diphenyl ethers; silicone oils; or mixtures thereof.

From the viewpoint of durability at high temperatures, synthetic oils are preferred, and polyol esters, polyphenyl ethers, and alkyl diphenyl ethers are more preferred.

It is desirable that the dynamic viscosity of these lubricant base oils at 100° C. is 2 to 40 mm$^2$/s and preferably 3 to 20 mm$^2$/s. Additionally, it is desirable that the viscosity index of the base oils is 90 or higher and preferably 100 or higher.

In this context, the grease composition according to this embodiment, unless its properties are impaired, may contain thickening agents other than the imide compound represented by the above general formula (1), solid lubricants, extreme pressure agents, antioxidants, oiliness agents, rust inhibitors, viscosity index enhancers, detergent dispersants, and the like as required in order to further improve its performance.

As the thickening agents other than the imide compound represented by the above general formula (1), any thickening agents, including soap thickening agents, such as metal soaps and complex metal soaps; and non-soap thickening agents, such as Benton, silica gel, urea compounds, urea-urethane compounds, and urethane compounds can be used. Examples of the soap thickening agents include sodium soaps, calcium soaps, aluminum soaps, and lithium soaps. Additionally, examples of the urea compounds, the urea-urethane compounds, and the urethane compounds include diurea compounds, triurea compounds, tetraurea compounds, other polyurea compounds, urea-urethane compounds, diurethane compounds or mixtures thereof. Furthermore, imide compounds other than the imide compound represented by the above general formula (1) may be contained.

Examples of the solid lubricants specifically include graphite, carbon black, graphite fluoride, polytetrafluoroethylene, molybdenum disulfide, antimony sulfide, and alkaline (earth) borates.

Examples of the extreme pressure agents specifically include organic zinc compounds, such as zinc dialkyldithiophosphates and zinc diaryldithiophosphates; sulfur-containing compounds, such as dihydrocarbyl polysulfide, sulfurized esters, thiazole compounds, and thiadiazole compounds; phosphates, and phosphites.

Examples of the antioxidants specifically include phenolic compounds, such as 2,6-di-t-butylphenol, and 2,6-di-t-butyl-p-cresol; amine compounds, such as dialkyldiphenylamines, phenyl-α-naphthylamines, and p-alkylphenyl-α-naphthylamines; sulphur compounds; and phenothiazine compounds.

Examples of the oiliness agents specifically include amines, such as laurylamine, myristylamine, palmitylamine, stearylamine, and oleylamine; higher alcohols, such as lauryl alcohol, myristyl alcohol, palmityl alcohol, stearyl alcohol, and oleyl alcohol; fatty esters, such as methyl laurate, methyl myristate, methyl palmitate, methyl stearate, and methyl oleate; amides, such as lauryl amide, myristyl amide, palmityl amide, stearyl amide, and oleyl amide; and oils and fats.

Examples of the rust inhibitors specifically include metal soaps; polyhydric alcohol partial esters, such as sorbitan fatty acid esters; amines; phosphoric acid; and phosphates.

Examples of the viscosity index enhancers specifically include polymethacrylates, polyisobutylene, and polystyrene.

Examples of the detergent dispersants specifically include sulphonates, salicylates, and phenates.

To prepare a grease composition according to this embodiment, the compound can be obtained by, for example, mixing and stirring the imide compound and additionally other additives as required with a base oil, and passing the mixture through a roll mill and the like. Alternatively, after the imide compound is prepared by preliminarily adding, melting, stirring and mixing raw material components of the imide compound of the thickening agent with a base oil, the grease composition can be also produced by further mixing and stirring the imide compound with other additives as required and passing the mixture through a roll mill and the like.

Since the grease composition according to the fourth embodiment is excellent in heat resistance, it is particularly preferably used as grease for constant velocity gears, variable velocity gears, automobiles, steelmaking facilities, industrial machines, precision machines, ball bearings, roller bearings, and the like to be used at high temperatures. The operating temperatures for these applications are preferably −40° C. to 300° C., and more preferably −40° C. to 250° C.

EXAMPLES

Hereinafter, the present invention will be described more specifically based on examples and comparative examples, but is not limited to any of the following examples.

Example 1

In 150 mL of NMP (N-methyl-2-pyrrolidone) solvent, 32.7 g of pyromellitic dianhydride represented by the following formula (6) and 15.0 g of diaminodiphenyl ether represented by the following formula (7) were reacted for one hour at room temperature. Subsequently, after 30 mL of toluene was added and heated for one hour at 180° C., 27.8 g of laurylamine represented by the formula (8) was added and stirred for one hour, and 30 mL of toluene was further added and heated for four hours at 180° C. to obtain a precipitate. The obtained precipitate was filtered and washed with 170 mL of toluene and 230 mL of acetone, and dried to obtain the imide compound-1 containing the imide compound represented by the following formula (9) as a solid (yield: 58.8 g).

[Chemical Formula 13]

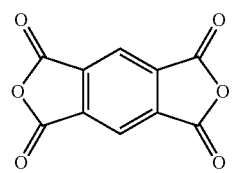

(6)

[Chemical Formula 14]

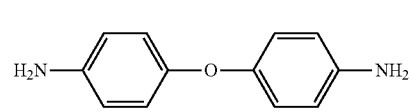

(7)

[Chemical Formula 15]

C$_{12}$H$_{25}$NH$_2$ (8)

[Chemical Formula 16]

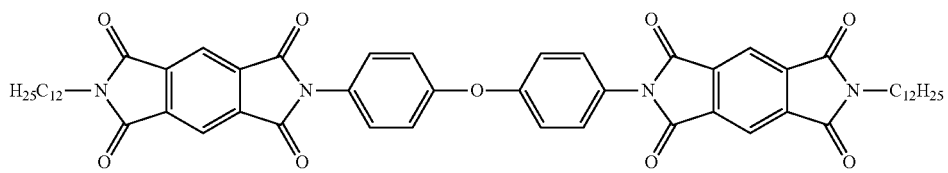
(9)

The infrared absorption spectrum (FT/IR-410, JASCO Corporation) of the imide compound-1 was measured by the KBr method. The result is shown in FIG. 1. As shown in FIG. 1, absorbance at about 1720 cm$^{-1}$ and about 1780 cm$^{-1}$ derived from cyclic imide groups were determined, but absorbance attributed to the reaction raw materials and absorbance at about 1650 cm$^{-1}$ derived from amide groups of the reaction intermediate were not determined. From this result, it was confirmed that the obtained solid was an imide compound and that imidization progressed to almost 100%.

Additionally, when FD-MS measurement (JMS-T100GC, JEOL Ltd., ionization method: FD+, solvent: o-n-propyl phenol) was performed on the imide compound-1, the peak attributed to the imide compound represented by the formula (9) was 47% relative to the total ion intensity.

Examples 2 to 15

In each of Examples 2 to 15, imide compounds-2 to 15 were obtained as solids as in Example 1, except that the compounds represented by the above formulas (6) to (8) or the following formulas (10) to (17) were used as the tetracarboxylic dianhydride represented by the general formula (2), the diamine represented by the general formula (3), and the monoamine represented by the general formula (5) in accordance with the combinations shown in Tables 1 to 5. The yields of the imide compounds-2 to 15 obtained are shown in Tables 1 to 5.

[Chemical Formula 17]

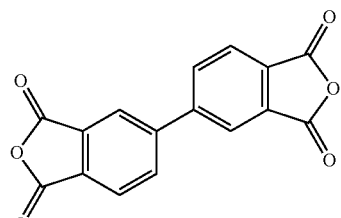
(10)

[Chemical Formula 18]

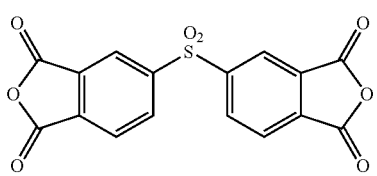
(11)

[Chemical Formula 19]

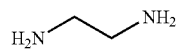
(12)

[Chemical Formula 20]

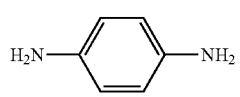
(13)

[Chemical Formula 21]

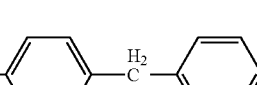
(14)

[Chemical Formula 22]

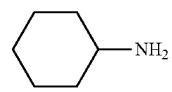
(15)

[Chemical Formula 23]

C$_{18}$H$_{37}$NH$_2$ (16)

[Chemical Formula 24]

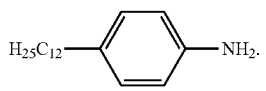
(17)

When the infrared absorption spectra were measured as in Example 1 on the imide compounds-2 to 15 obtained in Examples 2 to 15, absorbance at about 1720 cm$^{-1}$ and about 1780 cm$^{-1}$ derived from cyclic imide groups were determined for any of the compounds, but absorbance attributed to the reaction raw materials and absorbance at about 1650 cm$^{-1}$ derived from amide groups of the reaction intermediate were not determined. From these results, it was confirmed that the solids obtained in Examples 2 to 15 were imide compounds and that imidization progressed to almost 100%.

Additionally, when FD-MS measurement was performed as in Example 1 on the imide compounds-2 to 15 obtained in Examples 2 to 15, peaks attributed to the imide compounds shown in Tables 1 to 5 (any of the formulas (9), (18) to (29)) as the contained imide compounds were observed. The intensity ratios observed in each Example are shown in Tables 1 to 5 relative to the total ion intensity of the contained imide compound.

[Chemical Formula 25]
(18)
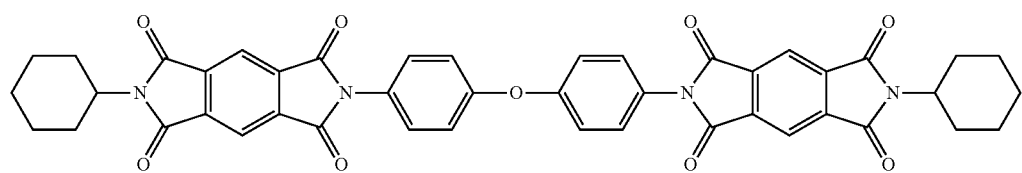
[Chemical Formula 26]
(19)
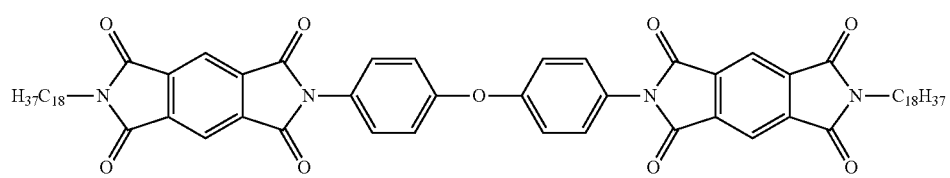
[Chemical Formula 27]
(20)
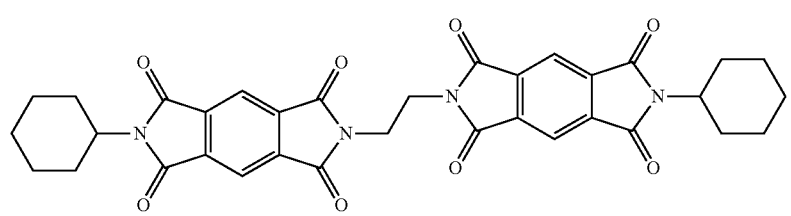
[Chemical Formula 28]      [Chemical Formula 29]
(21)      (22)
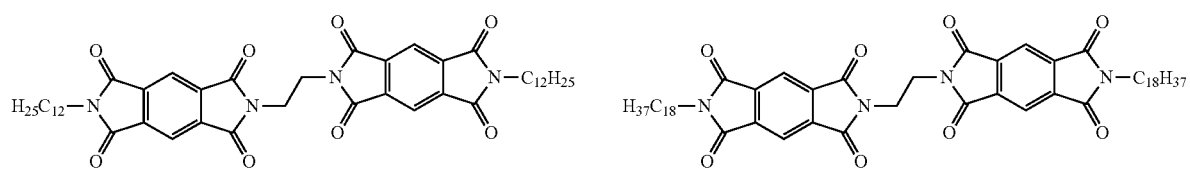
[Chemical Formula 30]
(23)
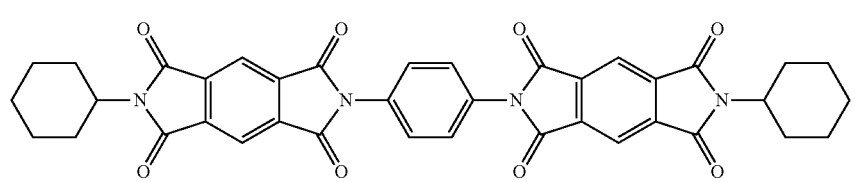
[Chemical Formula 31]
(24)
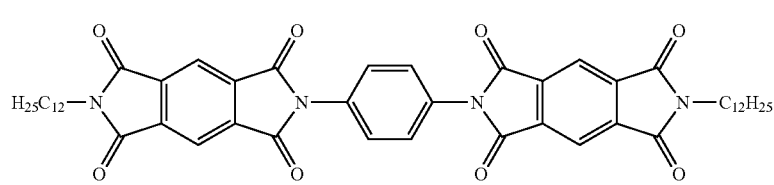
[Chemical Formula 32]
(25)
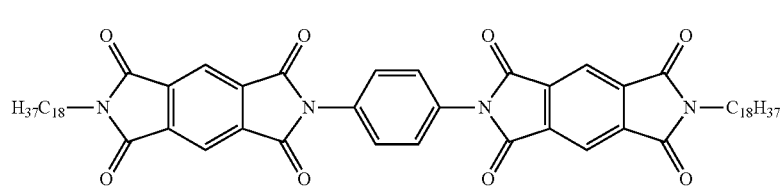

[Chemical Formula 33]

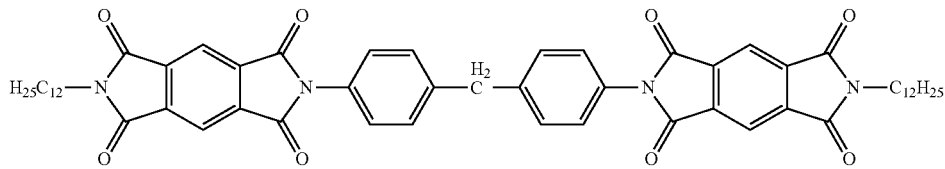

(26)

[Chemical Formula 34]

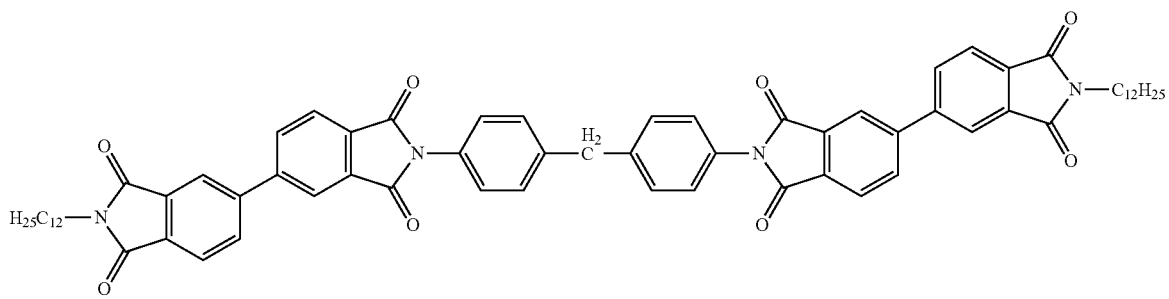

(27)

[Chemical Formula 35]

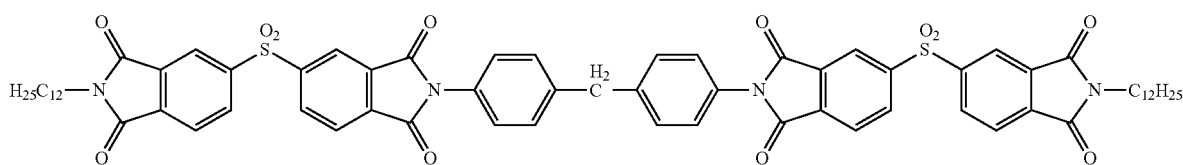

(28)

[Chemical Formula 36]

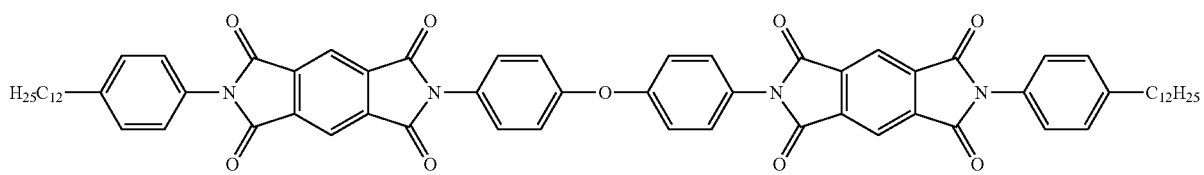

(29)

Comparative Example 1

In 300 g of diphenyl ether base oil with a 100° C. dynamic viscosity of 13 mm²/s, 4.2 g of cyclohexylamine was reacted with 55.8 g of diphenylmethane-4,4'-diisocyanate to obtain a grease-like material. The diphenyl ether base oil was removed from the grease-like material with hexane to obtain a urea compound represented by the formula (30). The yield of the urea compound-1 obtained is shown in Table 6.

[Chemical Formula 37]

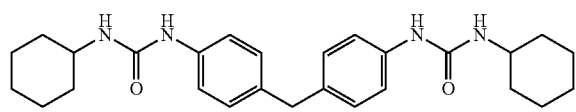

(30)

Comparative Example 2

In 300 g of diphenyl ether base oil with a 100° C. dynamic viscosity of 13 mm²/s, 68.3 g of octadecylamine was reacted with 31.7 g of diphenylmethane-4,4'-diisocyanate to obtain a grease-like material. The diphenyl ether base oil was removed from the grease-like material with hexane to obtain a urea compound represented by the formula (31). The yield of the urea compound-2 obtained is shown in Table 6.

[Chemical Formula 38]

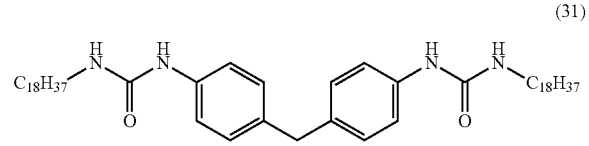

(31)

Comparative Example 3

In 315.3 g of diphenyl ether base oil with a 100° C. dynamic viscosity of 13 mm²/s, 74.2 g of p-dodecylaniline was reacted with 30.9 g of pyromellitic dianhydride to obtain a grease-like material. In this case, the synthesis was performed so that the concentration of reaction product in the grease-like material was 25% by weight. The diphenyl ether base oil was removed from the grease-like material with hexane to obtain an imide compound-16 represented by the formula (32). The yield of the imide compound obtained is shown in Table 6.

[Chemical Formula 39]

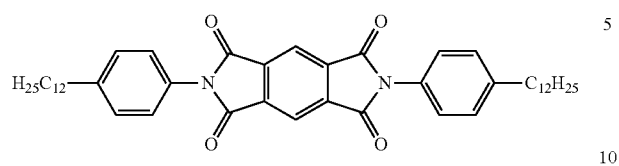

(32)

TABLE 1

|  |  |  | Example 1 | Example 2 | Example 3 |
|---|---|---|---|---|---|
| Imide compound |  |  | Imide compound-1 | Imide compound-2 | Imide compound-3 |
| Contained imide compound |  |  | Formula (9) | Formula (18) | Formula (19) |
| Tetracarboxylic dianhydride | Pyromellitic dianhydride (6) | g | 32.7 | 32.7 | 32.7 |
| Diamine | Diaminodiphenyl ether (7) | g | 15.0 | 15.0 | 15.0 |
| Monoamine | Cyclohexylamine (15) | g | — | 14.9 | — |
|  | Laurylamine (8) | g | 27.8 | — | — |
|  | Octadecylamine (16) | g | — | — | 40.4 |
|  | Yield | g | 58.8 | 50.9 | 64.3 |
|  | Ion intensity | % | 47 | 42 | 40 |

TABLE 2

|  |  |  | Example 4 | Example 5 | Example 6 |
|---|---|---|---|---|---|
| Imide compound |  |  | Imide compound-4 | Imide compound-5 | Imide compound-6 |
| Contained imide compound |  |  | Formula (20) | Formula (21) | Formula (22) |
| Tetracarboxylic dianhydride | Pyromellitic dianhydride (6) | g | 32.7 | 32.7 | 32.7 |
| Diamine | Ethylenediamine (12) | g | 4.5 | 4.5 | 4.5 |
| Monoamine | Cyclohexylamine (15) | g | 14.9 | — | — |
|  | Laurylamine (8) | g | — | 27.8 | — |
|  | Octadecylamine (16) | g | — | — | 40.4 |
| Yield |  | g | 40.1 | 51.9 | 57.9 |
| Ion intensity |  | % | 51 | 47 | 45 |

TABLE 3

|  |  |  | Example 7 | Example 8 | Example 9 |
|---|---|---|---|---|---|
| Imide compound |  |  | Imide compound-7 | Imide compound-8 | Imide compound-9 |
| Contained imide compound |  |  | Formula (23) | Formula (24) | Formula (25) |
| Tetracarboxylic dianhydride | Pyromellitic dianhydride (6) | g | 32.7 | 32.7 | 32.7 |
| Diamine | Phenylenediamine (13) | g | 8.1 | 8.1 | 8.1 |
| Monoamine | Cyclohexylamine (15) | g | 14.9 | — | — |
|  | Laurylamine (8) | g | — | 27.8 | — |
|  | Octadecylamine (16) | g | — | — | 40.4 |
| Yield |  | g | 42.2 | 56.4 | 71.1 |
| Ion intensity |  | % | 58 | 44 | 39 |

TABLE 4

|  |  |  | Example 10 | Example 11 | Example 12 |
|---|---|---|---|---|---|
| Imide compound |  |  | Imide compound-10 | Imide compound-11 | Imide compound-12 |
| Contained imide compound |  |  | Formula (26) | Formula (27) | Formula (28) |
| Tetracarboxylic | Pyromellitic dianhydride (6) | g | 32.7 | — | — |

TABLE 4-continued

|  |  |  | Example 10 | Example 11 | Example 12 |
|---|---|---|---|---|---|
| dianhydride | Biphenyltetracarboxylic dianhydride (10) | g | — | 44.1 | — |
|  | Bis(carboxyphenyl)sulfone tetracarboxylic dianhydride (11) | g | — | — | 53.7 |
| Diamine | Diaminodiphenylmethane (14) | g | 14.9 | 14.9 | 14.9 |
| Monoamine | Laurylamine (8) | g | 27.8 | 27.8 | 27.8 |
| Yield |  | g | 60.5 | 71.7 | 79.2 |
| Ion intensity |  | % | 46 | 46 | 40 |

TABLE 5

|  |  |  | Example 13 | Example 14 | Example 15 |
|---|---|---|---|---|---|
| Imide compound |  |  | Imide compound-13 | Imide compound-14 | Imide compound-15 |
| Contained imide compound |  |  | Formula (29) | Formula (9) | Formula (9) |
| Tetracarboxylic dianhydride | Pyromellitic dianhydride (6) | g | 32.7 | 34.3 | 40.9 |
| Diamine | Diaminodiphenyl ether (7) | g | 15.0 | 15.0 | 15.0 |
| Monoamine | Laurylamine (8) | g | — | 30.6 | 41.7 |
|  | p-dodecylaniline (17) | g | 39.2 | — | — |
| Yield |  | g | 74 | 69.1 | 82.2 |
| Ion intensity |  | % | 36 | 30 | 11 |

TABLE 6

|  |  |  | Comparative Example 1 | Comparative Example 2 | Comparative Example 3 |
|---|---|---|---|---|---|
| Urea compound or imide compound |  |  | Urea compound-1 | Urea compound-2 | Imide compound-16 |
| Contained urea compound or contained imide compound |  |  | Formula (30) | Formula (31) | Formula (32) |
| Tetracarboxylic dianhydride | Pyromellitic dianhydride (6) | g | — | — | 30.9 |
| Diisocyanate | Diphenylmethane diisocyanate | g | 55.8 | 31.7 | — |
| Monoamine | Cyclohexylamine (15) | g | 44.2 | — | — |
|  | Octadecylamine (16) | g | — | 68.3 | — |
|  | p-dodecylaniline (17) | g | — | — | 74.2 |
| Yield |  | g | 96.5 | 94.4 | 92.8 |

[Heat Resistance Evaluation]

Each about 0.2 g of the imide compounds-1 to 15 obtained in Examples 1 to 15, the imide compound-16 obtained in Comparative Example 3, and the urea compounds-1 and 2 obtained in Comparative Examples 1 and 2 was weighed into each screw bottle and left heated in an air thermostat at 200° C. for 300 hours. The weight after 300 hours was measured. The results obtained are shown in Tables 7 to 12. In Tables, it means that the smaller the decrease in weight, the more excellent in heat resistance.

[Thickening Power Evaluation]

Each of the imide compounds-1 to 15 obtained in Examples 1 to 15, the imide compound-16 obtained in Comparative Example 3, and the urea compounds-1 and 2 obtained in Comparative Examples 1 and 2 was mixed into diphenyl ether base oil with a dynamic viscosity of 13 mm$^2$/s to be 25% by weight. The compounds were passed through a roll mill to obtain materials uniformly dispersed in the base oil. The obtained materials were measured for their penetrations and dropping points after worked 60 times (60W) in accordance with JIS 2220, Determination of cone penetration. The results obtained are shown in Tables 7 to 12. In this case, for the urea compounds in Comparative Examples 1 and 2, penetrations were measured before removing the diphenyl ether base oil with hexane.

TABLE 7

|  |  | Example 1 | Example 2 | Example 3 |
|---|---|---|---|---|
| Imide compound |  | Imide compound-1 | Imide compound-2 | Imide compound-3 |
| Contained imide compound |  | Formula (9) | Formula (18) | Formula (19) |
| Heat resistance evaluation (Weight reduction rate, weight %) |  | 13.6 | 6.9 | 17.7 |
| Thickening power evaluation | Penetration | 272 | 377 | 272 |
|  | Dropping point (° C.) | >300 | >300 | >300 |

TABLE 8

|  | Example 4 | Example 5 | Example 6 |
|---|---|---|---|
| Imide compound | Imide compound-4 | Imide compound-5 | Imide compound-6 |

TABLE 8-continued

|  |  | Example 4 | Example 5 | Example 6 |
|---|---|---|---|---|
| Contained imide compound | | Formula (20) | Formula (21) | Formula (22) |
| Heat resistance evaluation (Weight reduction rate, weight %) | | 2.4 | 14.0 | 18.5 |
| Thickening power evaluation | Penetration | 320 | 322 | 299 |
| | Dropping point (° C.) | >300 | >300 | >300 |

TABLE 9

|  |  | Example 7 | Example 8 | Example 9 |
|---|---|---|---|---|
| Imide compound | | Imide compound-7 | Imide compound-8 | Imide compound-9 |
| Contained imide compound | | Formula (23) | Formula (24) | Formula (25) |
| Heat resistance evaluation (Weight reduction rate, weight %) | | 6.0 | 14.9 | 18.1 |
| Thickening power evaluation | Penetration | 331 | 259 | 264 |
| | Dropping point (° C.) | >300 | >300 | >300 |

TABLE 10

|  |  | Example 10 | Example 11 | Example 12 |
|---|---|---|---|---|
| Imide compound | | Imide compound-10 | Imide compound-11 | Imide compound-12 |
| Contained imide compound | | Formula (26) | Formula (27) | Formula (28) |
| Heat resistance evaluation (Weight reduction rate, weight %) | | 14.1 | 13.3 | 13.8 |
| Thickening power evaluation | Penetration | 268 | 228 | 260 |
| | Dropping point (° C.) | >300 | >300 | >300 |

TABLE 11

|  |  | Example 13 | Example 14 | Example 15 |
|---|---|---|---|---|
| Imide compound | | Imide compound-13 | Imide compound-14 | Imide compound-15 |
| Contained imide compound | | Formula (29) | Formula (9) | Formula (9) |
| Heat resistance evaluation (Weight reduction rate, weight %) | | 12.4 | 15.1 | 18.6 |
| Thickening power evaluation | Penetration | 332 | 273 | 280 |
| | Dropping point (° C.) | >300 | >300 | 288 |

TABLE 12

|  |  | Comparative Example 1 | Comparative Example 2 | Comparative Example 3 |
|---|---|---|---|---|
| Imide compound | | Urea compound-1 | Urea compound-2 | Imide compound-16 |
| Contained imide compound | | Formula (30) | Formula (31) | Formula (32) |
| Heat resistance evaluation (Weight reduction rate, weight %) | | 36.1 | 27.9 | 20.2 |
| Thickening power evaluation | Penetration | 221 | 225 | 338 |
| | Dropping point (° C.) | 280 | 272 | 220 |

From the results shown in Tables 7 to 12, it is found that the imide compounds-1 to 15 are more excellent in heat resistance than the urea compounds-1 and 2 obtained in Comparative Examples 1 and 2 and the imide compound 16 obtained in Comparative Example 3, and that they can be used as thickening agents for grease.

The invention claimed is:

1. An imide compound represented by the following formula (1):

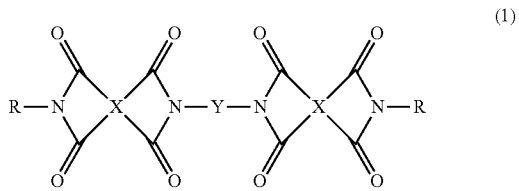

(1)

wherein X represents a tetravalent residue obtained by removing four carboxylic groups from a pyromellitic acid, Y represents a divalent residue obtained by removing two amino groups from compounds in which amino groups are bound to both ends of a linear aliphatic hydrocarbon having a carbon number of 2 to 10, compounds having two aminophenyl groups, or phenylenediamines, and R represents a residue obtained by removing an amino group from a cyclohexylamine.

2. A method for producing an imide compound comprising:

reacting an aromatic tetracarboxylic dianhydride represented by the following formula (2) with a diamine represented by the following formula (3) to obtain a reaction intermediate represented by the following formula (4); and reacting the reaction intermediate with a monoamine represented by the following formula (5) to obtain the imide compound represented by the following formula (1):

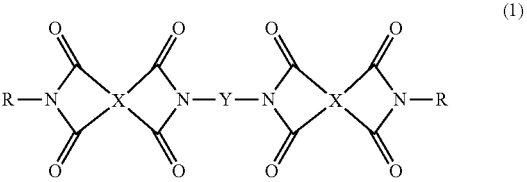

(1)

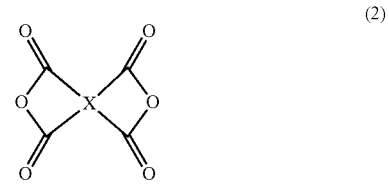

(2)

(3)

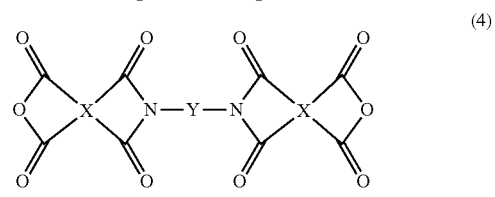

(4)

R—NH$_2$ (5)

wherein X represents a tetravalent residue obtained by removing four carboxylic groups from a pyromellitic acid, Y represents a divalent residue obtained by removing two amino groups from compounds in which amino groups are bound to both ends of a linear aliphatic hydrocarbon having a carbon number of 2 to 10, compounds having two aminophenyl groups, or phenylenediamines, and R represents a residue obtained by removing an amino group from a cyclohexylamine.

3. A thickening agent for a grease comprising at least one imide compound, wherein the imide compound according to claim 1 is present in an amount of 30% by mass or more of the total mass of the at least one imide compound, wherein the thickening agent provides increased heat resistance when subjected to a temperature of 200° C. for 300 hours as compared to the thickening agent in the absence of the imide compound.

4. A grease composition comprising a lubricant base oil and 2 to 50% by mass of the imide compound according to claim 1 based on the total mass of the grease composition.

* * * * *